United States Patent
Boone et al.

(10) Patent No.: US 10,463,285 B2
(45) Date of Patent: Nov. 5, 2019

(54) HERMETICALLY-SEALED PACKAGE AND METHOD OF FORMING SAME

(71) Applicant: Medtronic, Inc., Minneapolis, MN (US)

(72) Inventors: Mark R Boone, Gilbert, AZ (US); Jonathan L Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 232 days.

(21) Appl. No.: 15/477,904

(22) Filed: Apr. 3, 2017

(65) Prior Publication Data
US 2018/0279932 A1 Oct. 4, 2018

(51) Int. Cl.
*A61B 5/1455* (2006.01)
*F21V 31/00* (2006.01)
(Continued)

(52) U.S. Cl.
CPC ........ *A61B 5/14551* (2013.01); *A61B 5/0031* (2013.01); *A61B 5/0086* (2013.01); *A61B 5/0261* (2013.01); *A61B 5/02433* (2013.01); *A61B 5/0816* (2013.01); *A61B 5/14546* (2013.01); *A61N 1/059* (2013.01); *A61N 1/0563* (2013.01); *A61N 1/0587* (2013.01); *A61N 1/37518* (2017.08); *A61N 1/39* (2013.01); *F21V 3/00* (2013.01); *F21V 9/00* (2013.01); *F21V 23/06* (2013.01); *F21V 31/005* (2013.01); *F21Y 2115/10* (2016.08)

(58) Field of Classification Search
CPC . A61B 5/14551; A61B 5/0031; A61B 5/0086; A61B 5/02433; A61B 5/0261; A61B 5/0816; A61B 5/14546; A61N 1/39; A61N 1/0563; A61N 1/059; A61N 1/37518; F21V 3/00; F21V 23/06; F21V 21/005; F21Y 2115/05
See application file for complete search history.

(56) References Cited

U.S. PATENT DOCUMENTS 5,902,326 A 5/1999 Lessar et al.
6,125,290 A 9/2000 Miesel
(Continued)

OTHER PUBLICATIONS

Day, John K. et al, Sealed Pacakage Including Electronic Device and Power Source, U.S. Appl. No. 15/299,941, filed Oct. 21, 2016, 38 pages.

*Primary Examiner* — Boniface N Nganga

(57) ABSTRACT

Various embodiments of a sealed package and a method of forming such package are disclosed. The package includes a housing, a substrate hermetically sealed to the housing, and a light source disposed on a first major surface of the substrate. The package further includes a detector disposed on the first major surface of the substrate and having a detecting surface. The package also includes a masking layer disposed on at least one of the first major surface and a second major surface of the substrate, where the masking layer includes a first aperture aligned with an emission axis of the light source in a direction orthogonal to the first major surface of the substrate. The masking layer further includes a second aperture aligned with a detection axis of the detector in a direction orthogonal to the first major surface of the substrate.

14 Claims, 8 Drawing Sheets

(51) Int. Cl.
*A61B 5/00* (2006.01)
*A61B 5/145* (2006.01)
*F21V 9/00* (2018.01)
*F21V 3/00* (2015.01)
*F21V 23/06* (2006.01)
*A61B 5/024* (2006.01)
*A61B 5/026* (2006.01)
*A61B 5/08* (2006.01)
*A61N 1/39* (2006.01)
*A61N 1/05* (2006.01)
*A61N 1/375* (2006.01)
*F21Y 115/10* (2016.01)

(56) References Cited

U.S. PATENT DOCUMENTS

| | | |
|---|---|---|
| 6,125,291 A | 9/2000 | Miesel et al. |
| 6,134,459 A | 10/2000 | Roberts et al. |
| 6,583,445 B1 | 6/2003 | Reedy et al. |
| 6,586,776 B1 | 7/2003 | Liu |
| 7,653,434 B1 | 1/2010 | Turcott et al. |
| 8,090,432 B2 | 1/2012 | Cinbis et al. |
| 8,170,636 B2 | 5/2012 | Cinbis |
| 8,216,134 B2 | 7/2012 | Ries et al. |
| 8,275,432 B2 | 9/2012 | Kuhn et al. |
| 8,275,435 B2 | 9/2012 | Kuhn et al. |
| 8,290,557 B2 | 10/2012 | Davis et al. |
| 8,320,984 B2 | 11/2012 | Kuhn et al. |
| 8,346,332 B2 | 1/2013 | Kuhn et al. |
| 8,352,008 B2 | 1/2013 | Kuhn et al. |
| 8,391,979 B2 | 3/2013 | Kuhn et al. |
| 8,406,836 B2 | 3/2013 | Kuhn et al. |
| 8,452,402 B2 | 5/2013 | Ecker et al. |
| 8,458,543 B2 | 6/2013 | Tung |
| 8,463,343 B2 | 6/2013 | Kuhn et al. |
| 8,463,345 B2 | 6/2013 | Kuhn et al. |
| 8,463,346 B2 | 6/2013 | Kuhn et al. |
| 8,489,164 B2 | 7/2013 | Kuhn |
| 8,489,168 B2 | 7/2013 | Kuhn et al. |
| 8,515,537 B2 | 8/2013 | Cinbis et al. |
| 8,521,245 B2 | 8/2013 | Kuhn |
| 8,548,543 B2 | 10/2013 | Cinbis et al. |
| 8,571,620 B2 | 10/2013 | Cinbis et al. |
| 8,577,436 B2 | 11/2013 | Baker, Jr. |
| 8,630,708 B2 | 1/2014 | Kuhn et al. |
| 8,634,890 B2 | 1/2014 | Kuhn et al. |
| 8,639,332 B2 | 1/2014 | Kuhn et al. |
| 8,664,756 B2 | 3/2014 | Boone et al. |
| 8,666,466 B2 | 3/2014 | Kuhn et al. |
| 8,781,547 B2 | 7/2014 | Kuhn |
| 8,795,595 B2 | 8/2014 | Shah |
| 8,918,171 B2 | 12/2014 | Kuhn et al. |
| 9,044,181 B2 | 6/2015 | Kuhn et al. |
| 9,126,049 B2 | 9/2015 | Kuhn et al. |
| 9,326,711 B2 | 5/2016 | Kracker et al. |
| 2007/0156085 A1 | 7/2007 | Schulhauser et al. |
| 2008/0208020 A1* | 8/2008 | Cinbis ............... A61B 5/0059 600/323 |
| 2009/0076353 A1* | 3/2009 | Carpenter .......... A61B 5/14546 600/310 |
| 2009/0156912 A1* | 6/2009 | Kuhn .................. A61B 5/0086 600/310 |
| 2009/0156918 A1 | 6/2009 | Davis et al. |
| 2010/0022856 A1 | 1/2010 | Cinbis et al. |
| 2010/0030043 A1 | 2/2010 | Kuhn |
| 2010/0185262 A1 | 7/2010 | Kuhn et al. |
| 2010/0262208 A1 | 10/2010 | Parker |
| 2010/0317947 A1 | 12/2010 | Cinbis et al. |
| 2010/0318146 A1 | 12/2010 | Cinbis et al. |
| 2011/0066017 A1 | 3/2011 | Kuhn |
| 2013/0103124 A1* | 4/2013 | Imran .................. A61N 1/375 607/92 |
| 2013/0334680 A1 | 12/2013 | Boone et al. |
| 2014/0368266 A1 | 12/2014 | Askarinya et al. |
| 2015/0321011 A1 | 11/2015 | Carney et al. |
| 2015/0321012 A1 | 11/2015 | Cinbis et al. |
| 2016/0185081 A1 | 6/2016 | Sandlin et al. |
| 2016/0345872 A1 | 12/2016 | Wasson et al. |

* cited by examiner

HERMETICALLY-SEALED PACKAGE AND METHOD OF FORMING SAME

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators, and drug pumps, which include electronic circuitry and one or more power sources, require an enclosure or housing to contain and seal these elements within a body of a patient. Many of these IMDs include one or more electrical feedthrough assemblies to provide electrical connections between the elements contained within the housing and components of the IMD external to the housing, for example, one or more sensors, electrodes, and lead wires mounted on an exterior surface of the housing, or electrical contacts housed within a connector header, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically-sealed housing to contain electronic circuitry of the sensor and an electrical feedthrough assembly to provide electrical connection between one or more lead wires, which extend within the implantable lead body, and the contained circuitry.

IMDs for monitoring a physiological condition and/or delivering a therapy can include one or more physiological sensors. Such sensors can provide one or more signals related to one or more physiological conditions of a patient state. Examples of such IMDs include heart monitors, pacemakers, implantable cardioverter defibrillators (ICDs), myostimulators, neurological stimulators, drug delivery devices, insulin pumps, glucose monitors, etc.

Optical sensors may be employed in IMDs as physiological sensors configured to detect changes in light modulation by, for example, a body fluid or tissue measurement volume due to a change in a physiological condition in the body fluid or tissue. Such optical sensors can be used, for example, to detect changes in metabolite levels in the blood, such as oxygen saturation levels or glucose level, or changes in tissue perfusion. A typical optical sensor can include one or more light sources and one or more detectors that are adapted to detect light emitted by the light sources and modulated by, e.g., body fluid or tissue measurement volume.

Monitoring such physiological conditions provides useful diagnostic measures and may be used in managing therapies for treating a medical condition. For example, a decrease in blood oxygen saturation or in tissue perfusion may be associated with insufficient cardiac output or respiratory function. Thus, monitoring such conditions may allow an implantable medical device to respond to a decrease in oxygen saturation or tissue perfusion, for example, by delivering electrical stimulation therapies to the heart to restore a normal hemodynamic function.

SUMMARY

In general, the present disclosure provides various embodiments of a sealed package and a method of forming such package. The sealed package can include a housing and a substrate sealed to the housing. The package can also include one or more light sources and detectors disposed within the housing. In one or more embodiments, one or more of the light sources and one or more of the detectors can be disposed on a first major surface of the substrate that faces the interior of the housing. The sealed package can be implanted in any suitable location within the patient and utilized to detect a physiological condition of the patient. For example, the physiological condition can be detected by analyzing at least a portion of light emitted by the light source and modulated by scattering from tissue of the patient.

In one aspect, the present disclosure provides a hermetically-sealed package that includes a housing having an inner surface and an outer surface, a substrate hermetically sealed to the housing and having a first major surface and a second major surface, and a light source disposed on the first major surface of the substrate and having an emitting surface. The light source is adapted to emit light through the first and second major surfaces of the substrate. The package further includes a detector disposed on the first major surface of the substrate and having a detecting surface, where the detector is adapted to detect at least a portion of the light emitted by the light source. The package also includes a masking layer disposed on at least one of the first major surface and the second major surface of the substrate, where the masking layer includes a first aperture aligned with an emission axis of the light source in a direction orthogonal to the first major surface of the substrate. The masking layer further includes a second aperture aligned with a detection axis of the detector in a direction orthogonal to the first major surface of the substrate.

In another aspect, the present disclosure provides a hermetically-sealed package that includes a housing having an inner surface and an outer surface, a substrate hermetically sealed to the housing and having a first major surface and a second major surface, and a light source disposed on the first major surface of the substrate and having an emitting surface. The light source is adapted to emit light through the first and second major surfaces of the substrate. The package further includes a detector disposed on the first major surface of the substrate and having a detecting surface, where the detector is adapted to detect at least a portion of the light emitted by the light source, and a diffuse region disposed between the emission axis of the light source and the detection axis of the detector in a lateral direction parallel to the first major surface of the substrate.

In another aspect, the present disclosure provides a hermetically-sealed package that includes a housing having an inner surface and an outer surface, a substrate hermetically sealed to the housing and having a first major surface and a second major surface, and a light source disposed on the first major surface of the substrate and having an emitting surface. The light source is adapted to emit light through the first and second major surfaces of the substrate. The package further includes a detector disposed on the second major surface of the substrate and has a detecting surface, where the detector is adapted to detect at least a portion of the light emitted by the light source; a conductor disposed on the first major surface of the substrate, where the conductor is electrically connected to the light source; and a via disposed between the first major surface and the second major surface of the substrate, where the via is electrically connected to the detector and the conductor.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
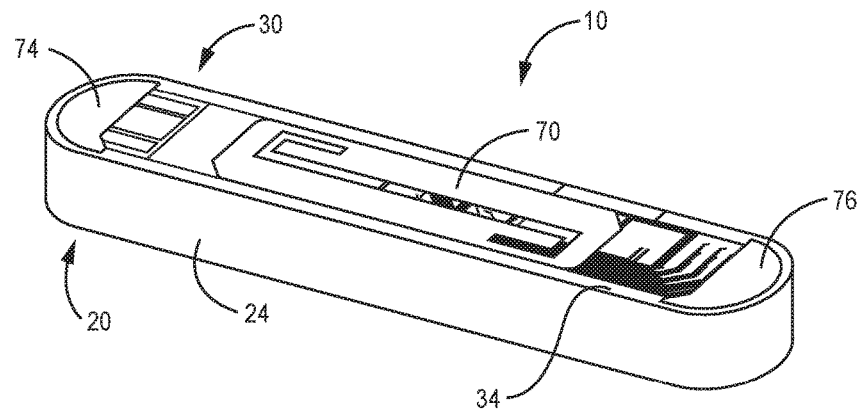
FIG. 1 is a schematic perspective view of one embodiment of a sealed package.

In general, the present disclosure provides various embodiments of a sealed package and a method of forming such package. The sealed package can include a housing and a substrate sealed to the housing. The package can also include one or more light sources and detectors disposed within the housing. In one or more embodiments, one or more of the light sources and one or more of the detectors can be disposed on a first major surface of the substrate that faces the interior of the housing. The sealed package can be implanted in any suitable location within the patient and utilized to detect a physiological condition of the patient. For example, the physiological condition can be detected by analyzing at least a portion of light emitted by the light source and modulated by scattering from tissue of the patient.

In one or more embodiments, the package can also include one or more optical devices that can reduce the amount of light emitted by the light source that propagates along the substrate due to total internal reflection at boundaries between the substrate and adjacent elements or body fluids/tissue of the patient. Such propagating light can be incident upon a detecting surface of the detector and reduce one or both of the quality and magnitude of a signal produced by the detector as such light has not been incident upon body fluid or tissue of the patient. The one or more optical devices can include any suitable layer, region, or optical element such as a masking layer or a diffuse region. Further, the one or more optical devices can utilize any suitable technique or techniques for preventing undesirable light from reaching the detector, e.g., absorption, scattering, etc.

The various embodiments of sealed packages described herein can be utilized for remote patient diagnostics, monitoring, and treatment with any suitable system. For example, one or more embodiments of sealed packages described herein can include an implantable medical device or system disposed within the sealed package. In one or more embodiments, the sealed package can be electrically connected to an implantable medical device. Nearly any implantable medical device or system employing leads may be used in conjunction with the various embodiments of sealed packages described herein. Representative examples of implantable medical devices included in or utilized with the various embodiments of sealed packages described herein include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators, ventricular assist devices; or the like.

Recently, health care costs have dramatically risen in part from the increased incidence of chronic diseases such as heart failure, sleep apnea, and chronic obstructive pulmonary disease (COPD), and interactions of such. These chronic diseases are often managed in a cyclic response to symptoms, i.e., the patient becomes increasingly symptomatic, goes to the clinician, and the clinician diagnoses and treats the condition. Clinician visits, however, are expensive. Further, the cost to treat such patients increases significantly with worsening symptoms. On the other hand, prevention along with adequate warnings given to the patient can be much less expensive.

Currently, clinicians gather and assimilate a wealth of information to diagnose and manage patients. Such information can be gathered using lab work, in-office biomedical measurements, and direct observations and information from the patient. Oftentimes, a trial treatment can be prescribed, and the efficacy of such treatment can be confirmed by observing the various responses of the patient to the treatment.

Previous attempts at providing chronically implantable detection devices such as optical sensors have proven to be challenging because of the high cost, large size, and relatively large number of components needed to form such detection devices. One purpose of using optical sensors in such chronically implantable settings is to better guide existing therapies and reduce clinical burdens.

One or more embodiments of sealed packages described herein that include one or more sensors (e.g., optical sensors) can provide a low-cost mechanism for providing remote measurements of one or more physiological conditions of a patient. An exemplary embodiment of a sealed package can provide earlier indications that a patient is trending toward a worsening condition prior to becoming symptomatic. Further, one or more embodiments of sealed packages described herein can enable low-power subcutaneous optical sensing at reduced cost and size over prior solutions. Such packages can also provide remote monitoring of any desired physiological condition, e.g., arterial oxygen, under controlled and repeatable conditions that can be difficult and cumbersome to reliably monitor with typical external devices.

Figure 2:
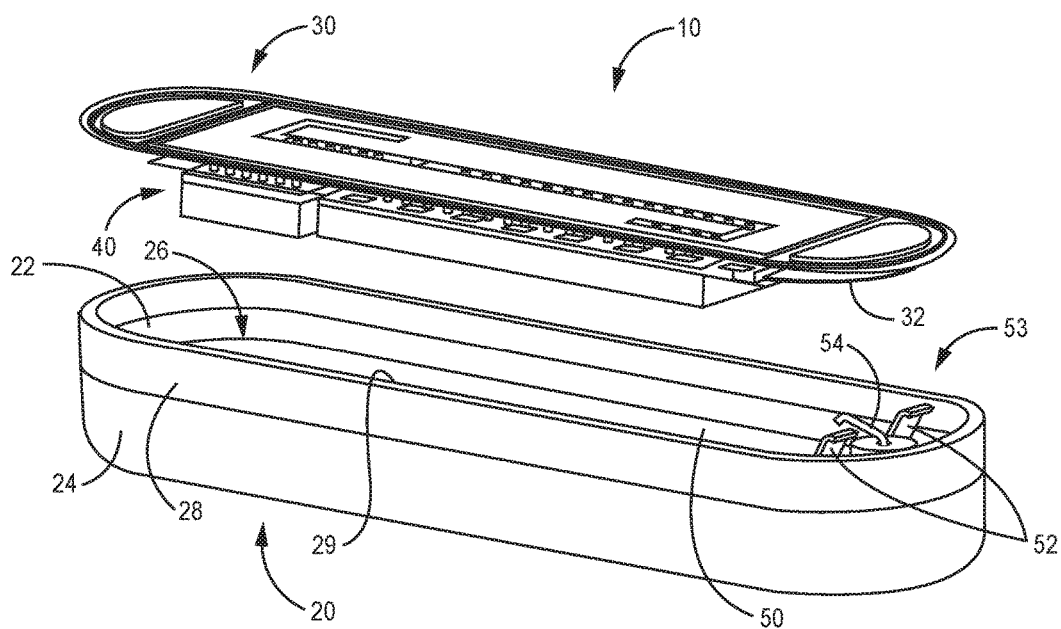
FIG. 2 is a schematic exploded view of the sealed package of FIG. 1.
Figure 3:
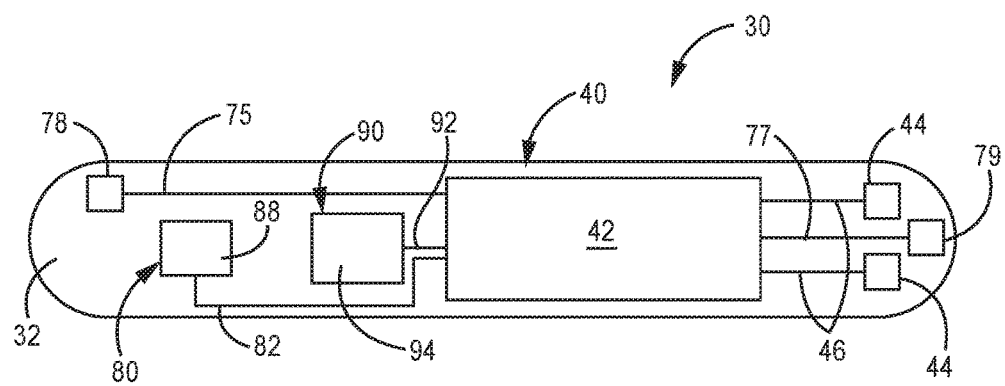
FIG. 3 is a schematic plan view of a first major surface of a substrate of the sealed package of FIG. 1.
Figure 4:
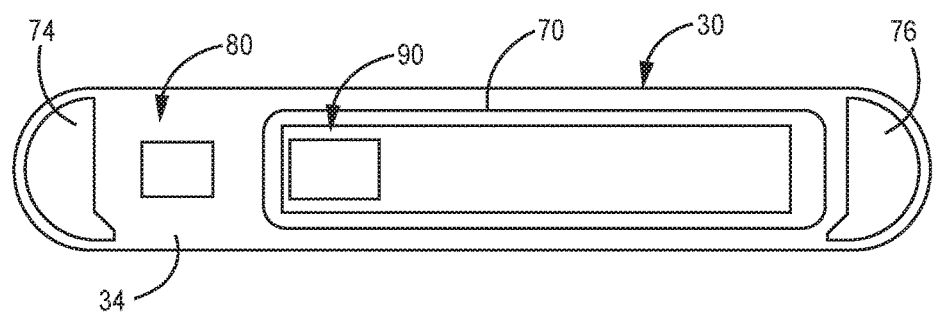
FIG. 4 is a schematic plan view of a second major surface of the substrate of the sealed package of FIG. 1.

FIGS. 1-5 are various schematic views of one embodiment of a sealed package 10. The package 10 includes a housing 20 and a substrate 30. The housing 20 includes an inner surface 22 and an outer surface 24. The substrate 30 can be a non-conductive substrate and includes a first major surface 32 and a second major surface 34. The package 10 can also include one or more electronic devices 40 disposed within the housing 10. For example, the electronic devices 40 can include a light source 80 (FIG. 3). In one or more embodiments, the light source 80 can be disposed on the first major surface 32 of the substrate 30. The light source 80 can be adapted to emit light through the first and second major surfaces 32, 34 of the substrate 30.

The electronic devices 40 can further include a detector 90 (FIG. 3). In one or more embodiments, the detector 90 can be disposed on the first major surface 32 of the substrate 30. The detector 90 can be adapted to detect the light emitted by the light source 80. Together, the light source 80 and the detector 90 can, in one or more embodiments, provide an optical sensor.

The package 10 also includes a power source 50 that is disposed at least partially within the housing 20. In one or more embodiments, the power source 50 can be disposed within a cavity 26 of the housing 20. The power source 50 can include any suitable power source or sources as is further described herein.

The substrate 30 can be sealed to the housing 20. In one or more embodiments, the substrate 30 can be hermetically sealed to the housing 20. The substrate 30 can be sealed to the housing 30 using any suitable techniques or techniques. In one or more embodiments, the substrate 30 can be hermetically sealed to the housing 20 by a laser bond.

The housing 20 can include any suitable material or materials, e.g., metallic, polymeric, ceramic, or inorganic materials. In one or more embodiments, the housing 20 can include at least one of glass, quartz, silica, sapphire, silicon carbide, diamond, and gallium nitride. In one or more embodiments, the housing 20 can include at least one of copper, silver, titanium, niobium, zirconium, tantalum, stainless steel, platinum, and iridium. The housing 20 can include the same material or combination of materials as the substrate 30. In one or more embodiments, the housing 20 can include one or more materials that are different from the material or materials of the substrate 30. Further, in one or more embodiments, the housing 20 can include biocompatible materials such that the package 10 can be implanted within a patient's body. For example, one or more coatings or layers can be disposed on the outer surface 24 of the housing 20 that provide biocompatibility. In one or more embodiments, the housing 20 can be electrically conductive to provide a ground electrode for the package 10 as is known in the art. In one or more embodiments, the housing 20 can be nonconductive.

Further, the housing 20 can take any suitable shape or combination of shapes and can have any suitable dimensions. In one or more embodiments, the housing 20 takes a shape that forms the cavity 26 that can accommodate the power source 50 (including active material and power source electronics) and one or more electronic devices 40 as is further described herein.

Sealed to the housing 20 is the substrate 30. In one or more embodiments, the substrate 30 can be a non-conductive or insulative substrate such that the electronic devices 40 (including light source 80 and detector 90), optional external electrodes 74, 76, and any conductors or other devices disposed on the substrate can be electrically isolated if desired. The substrate 30 can include any suitable material or materials. In one or more embodiments, the substrate 30 can include at least one of glass, quartz, silica, sapphire, silicon carbide, diamond, and gallium nitride. As with the housing 20, the substrate 30 can include a biocompatible material. For example, the substrate 30 can include one or more coatings or layers that can provide biocompatibility.

In one or more embodiments, the substrate 30 can be a transparent substrate. As used herein, the phrase "transparent substrate" refers to a substrate that can transmit a given percentage of light incident thereon during use of laser bonding techniques described herein to preferentially heat only an outer surface of the substrate (e.g., first major surface 32 or second major surface 34 of substrate 30), and not an inner bulk of the substrate, and thereby create a bond that has a relatively greater strength than the bulk strength of the substrate. Further, the transparent substrate 30 can transmit light emitted by the light source 80 having any suitable wavelength or combinations of wavelengths. The substrate 30 can be substantially transparent at a desired wavelength or range of wavelengths. As used herein, the phrase "substantially transparent" means that the substrate 30 transmits greater than 50% of light incident on the substrate for a selected wavelength or range of wavelengths, assuming no reflection at the air-substrate boundaries. In one or more embodiments, the substrate 30 can be substantially transmissive to light having a wavelength of at least 200 nm. In one or more embodiments, the substrate 30 can be substantially transmissive to light having a wavelength of greater than 10,000 nm. In one or more embodiments, the substrate 30 can be substantially transmissive to light having a wavelength in a range of 200 nm to 10,000 nm. In one or more embodiments, the substrate 30 can be substantially transmissive to at least one of UV light, visible light, and IR light.

In one or more embodiments, at least a portion of the substrate 30 can be transparent such that the detector 90 disposed on the first major surface 32 can detect one or more external signals, e.g., from a patient, when the package 10 is disposed within the patient. In one or more embodiments, the at least a portion of the substrate 30 can be sufficiently transparent to enable transmission of all, or a sufficient magnitude, of the light that is incident on the substrate for reception by the detector 90 such that the received light can be processed to detect the external signal. In one or more embodiments, the substrate 30 can be opaque, and a through-hole can be formed through the substrate and filled with a transparent hermetic material such as glass to provide a transparent portion of the substrate.

The substrate 30 can include any suitable dimensions, e.g., thicknesses. Further, the substrate 30 can take any suitable shape or combinations of shapes. In one or more embodiments, the substrate 30 can take a shape or combination of shapes that is complementary to a shape of the housing 20 such that the substrate can be sealed to the housing and provide a low-profile shape for the sealed package 10. Further, the substrate 30 can be a single, unitary substrate or multiple substrates joined together.

Disposed on the first major surface 32 of the substrate 30 are the electronic devices 40. Although depicted as being disposed on the first major surface 32, one or more electronic devices 40 can be disposed on the second major surface 34, or one or more electronic devices can be disposed on both the first and second major surfaces. In one or more embodiments, one or more electronic devices 40 can be disposed within the housing 20 and not connected to the substrate 30. The electronic devices 40 can include any suitable circuit or component, e.g., capacitors, transistors, integrated circuits, including controllers and multiplexers, sensors, light sources, detectors, accelerometers, signal processors, etc.

Further, any suitable technique or combination of techniques can be utilized to dispose one or more electronic devices 40 on the substrate 30 and/or within the cavity 26 of the housing 20. In one or more embodiments, one or more electronic devices 40 can be formed on the first major surface 32 of the substrate 30. In one or more embodiments, one or more devices 40 can be formed separately and then attached to the first major surface 32. Any suitable technique or techniques can be utilized to attach the electronic devices 40 to the substrate 30, e.g., a bond can be formed between the electronic device and the first major surface 32 of the substrate.

The electronic devices 40 can include one or more light sources 80. The light source 80 can include any suitable light source or combination of light sources. For example, the light source 80 can include any electrical circuit component(s) capable of emitting light in response to an applied voltage or current, including, for example, light emitting diodes (LEDs), laser diodes, vertical cavity surface emitting lasers (VCSELs), organic LEDs printed directly on the surface, nano-emitters, etc. The light source 80 can be a cluster of one or more components that emit one or more discrete wavelengths, or broadband emitters spanning a large range of wavelengths.

Although depicted as including a single light source 80, the device 10 can include any suitable number of light sources as is further described herein. The light source 80 can include an emitting surface 88. Although depicted as having one emitting surface 88, the light source 80 can include two or more emitting surfaces.

The light source 80 can be a packaged light source. In one or more embodiments, the light source 80 can include a flip-chip type package. In one or more embodiments, the light source 80 can be a bare semiconductor die.

The light source 80 can be adapted to emit light of any suitable wavelength or wavelengths. In one or more embodiments, the light source 80 can emit at least one of infrared, near-infrared, visible, and UV light. In one or more embodiments, the light source 80 can emit visible light having a wavelength of at least 350 nm and no greater than 850 nm. The light source 80 can emit any suitable bandwidth of light. In one or more embodiments, the light source 80 can emit light in a narrow band, e.g., the light source is adapted to emit light having an emission profile no greater than 20 nm, 15 nm, 10 nm, or 5 nm full-width at half-maximum (FWHM). In one or more embodiments, a narrow band source can be paired with a broadband detector that is sensitive to all of the wavelengths emitted by the source. In one or more embodiments, a narrow-band source can be paired with a narrow-band detector. Further, in one or more embodiments, a narrow band source can be paired with two or more broadband detectors. For example, silicon detectors can be sensitive in the visible to near-infrared wavelength ranges (e.g., up to about 1000 nm), but gallium arsenide can be sensitive to longer infrared wavelengths (e.g., greater than 1000 nm).

In one or more embodiments, the light source 80 can include a broadband emitter that utilizes re-emission of phosphorous materials or combination of broadband FWHM LEDs, e.g., a 680 nm LED with greater than a 50 nm FWHM that spans into the 720 nm wavelength. In such embodiments, a single LED can provide emission at both 680 nm and 720 nm, paired with a detector 90 that can discriminate between these two wavelengths. Similarly, a second broadband FWHM light source 80 can be used at 800 nm that also spans 760 nm. In such embodiments, two broadband FWHM LEDs can span four wavelengths, e.g., 680, 720, 760, and 800 nm and can be paired with a detector 90 that can detect all four wavelengths. In such embodiments, the detector 90 can include a narrow band pass filter or filters to detect the emitted light.

In one or more embodiments, the light source 80 can be adapted to emit light in one or more pulses having any suitable pulse width and periodicity. Further, in one or more embodiments, the light source 80 may be pulsed in a sequential manner.

The light source 80 can have any suitable cone angle of emission. As used herein, the term "cone angle" refers to solid angle relative to a normal to the surface of the emitter. In one or more embodiments, the light source 80 can have a cone angle of no greater than 90 degrees, 80 degrees, 70 degrees, 60 degrees, 50 degrees, 40 degrees, 30 degrees, 20 degrees, 10 degrees, or 5 degrees. In one or more embodiments, the light source 80 can include one or more optical elements that can direct light through the substrate 30 to increase light source efficiency and to prevent light from leaking into the interior of the housing 20, thereby causing interference with other components disposed within the housing.

In general, the number of light sources 80 and corresponding emission wavelengths utilized in the packages described herein can be selected according to the requirements of a particular application and will depend on the physiological condition or conditions being monitored.

Figure 5:
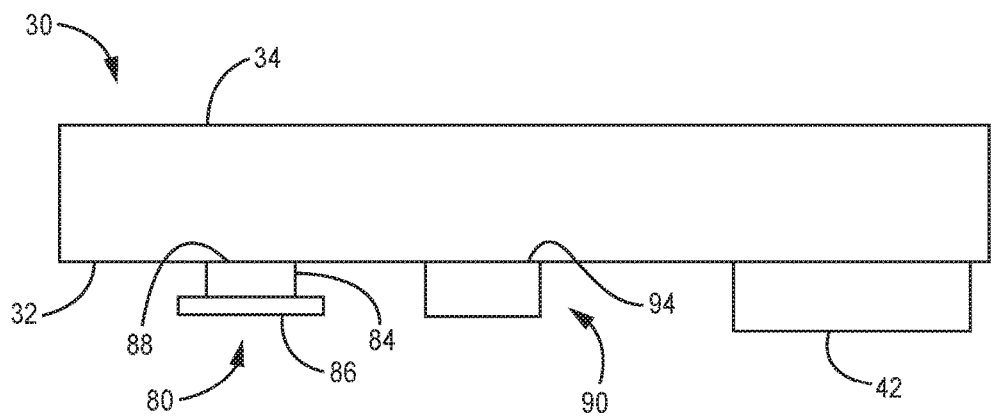
FIG. 5 is a schematic cross-section view of the substrate of the sealed package of FIG. 1.

The light source 80 can be disposed in any suitable location within the housing 20 of the device 10. In one or more embodiments, the light source 80 is disposed adjacent the first major surface 32 of the substrate 30. As used herein, the term "adjacent" means that an element or component is disposed closer to the first major surface 32 of the substrate 30 than to the power source 50 disposed within the housing 20. In one or more embodiments, the light source 80 can be disposed on the first major surface 32 of the substrate 30 as shown in FIG. 5 using any suitable technique or techniques. In such embodiments, an emitting surface 88 of the light source 80 can be connected to the first major surface 32 of the substrate 30 using any suitable technique. For example, in one or more embodiments, the emitting surface 88 can be disposed on the second major surface 32 of the substrate 30 using an optical coupling layer (not shown). Any suitable coupling layer can be utilized. In one or more embodiments, a refractive index of the optical coupling layer can be selected such that a substantial portion of the light emitted by the light source 80 is directed from the emitting surface 88 and into the substrate 30 without a substantial portion of the emitted light being reflected at a boundary between the emitting surface and the first major surface 32 of the substrate 30. In one or more embodiments, the optical coupling layer can include an optical adhesive.

The light source 80 can be electrically connected to one or more electronic devices 40 disposed on one or both of the first major surface 32 and second major surface 34 of the substrate 30 or within the housing 20 using any suitable technique or techniques. For example, the light source 80 can be electrically connected to a conductor 82 (FIG. 3) that is disposed on or within the substrate 30. The conductor 82 can electrically connect the light source 80 to a controller 42 of the electronic devices 40. Any suitable technique or techniques can be utilized to electrically connect the light source 80 to the conductor 82, e.g., bump bonding, solder reflow, conventional wire bonding, laser ribbon bonding, conductive epoxy bonding, etc.

The package 10 also includes the detector 90. The detector 90 includes a detecting surface 94 (FIG. 3). The detector 90 can include any suitable detector that is adapted to detect light emitted by the light source 80, e.g., one or more photodiodes, photoresistors or light dependent resistors, phototransistors, photovoltaic cells, charge-coupled devices, avalanche detectors, etc. In one or more embodiments, a light source 80 can also be utilized as a detector. Although depicted as including a single detector 90, the package 10 can include any suitable number of detectors as is further described herein.

The detector 90 can be adapted to detect any desired wavelength or wavelengths. In one or more embodiments, the detector 90 can detect one or more of infrared, near-infrared, visible, and UV light. In one or more embodiments, the detector 90 can detect visible light having a wavelength of at least 350 nm and no greater than 850 nm.

The detector 90 can be disposed in any suitable location within the housing 20 of the device 10 or outside of the housing (e.g., on the second major surface 34 of the substrate 30). In one or more embodiments, the detector 90 is disposed adjacent the first major surface 32 of the substrate 30. In one or more embodiments, the detector 90 can be disposed on the first major surface 32 of the substrate 30 using any suitable technique or techniques as shown in FIG. 5. In such embodiments, the detecting surface 94 can be connected to the first major surface 32 of the substrate 30 using any suitable technique. For example, in one or more embodiments, the detecting surface 94 can be disposed on the first major surface 32 of the substrate 30 using an optical coupling layer. Any suitable coupling layer can be utilized. In one or more embodiments, the optical coupling layer can include an optical adhesive. In one or more embodiments, the detector 90 can be electrically connected to an electrode disposed on a carrier. The detector 90 can also be wired bonded from the light source 80 to a second electrode on the carrier. The carrier can be designed such that the two electrodes are in a single plane. The carrier can then be bump-bonded to one or more conductors (e.g., conductor 92) disposed on the substrate 30.

The detector 90 can be electrically connected to one or more of the other electronic devices 40 disposed on one or both of the first major surface 32 and second major surface 34 of the substrate 30 or within the housing 20 using any suitable technique or techniques. For example, the detector 90 can be electrically connected to a conductor 92 that is disposed on or within the substrate 30. In one or more embodiments, the conductor 92 can electrically connect the detector 90 to the controller 42 of the electronic devices 40. Any suitable technique or techniques can be utilized to electrically connect the detector 90 to the conductor 92.

Figure 6:
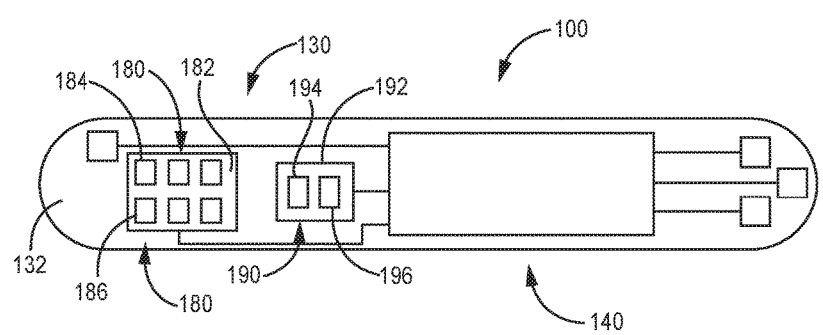
FIG. 6 is a schematic perspective view of a first major surface of a substrate of another embodiment of a sealed package.

As mentioned herein, the package 10 can include any suitable number of light sources 80 and detectors 90. For example, FIG. 6 is a schematic plan view of another embodiment of a sealed package 100. All of the design considerations and possibilities regarding the sealed package 10 of FIGS. 1-5 apply equally to the package 100 of FIG. 6. The package 100 includes a housing (not shown for clarity) and a substrate 130 hermetically sealed to the housing and including a first major surface 132 and a second major surface (not shown).

One difference between the package 100 of FIG. 6 and the package 10 of FIGS. 1-5 is that package 100 includes electronic devices 140 that include an array of light sources 180. The array 180 is disposed on a substrate 182. In one or more embodiments, the one or more light sources of the array 180 can be disposed on the substrate 182 or directly onto the first major surface 132 of the substrate 130 of the package 100.

The array 180 can include any suitable number of light sources. In the embodiment illustrated in FIG. 6, the array includes six light sources. Each of the light sources of the array 180 can have the same properties. In one or more embodiments, one or more light sources of the array 180 can have one or more properties that are different from the properties of one or more additional light sources of the array. For example, a first light source 184 of the array 180 can emit light having a first wavelength, and a second light source 186 of the array can emit light having a second wavelength that is the same as or different from the first wavelength. In one or more embodiments, the light sources of the array 180 can be independently addressable such that one or more of the light sources can be turned on or off independent from one or more additional light sources of the array.

Another difference between package 100 and package 10 is that the package 100 includes an array of detectors 190 having, in the illustrated embodiment, a first detector 194 and a second detector 196 disposed on a substrate 192. In one or more embodiments, the detector array 190 can include any suitable number of detectors. The detectors of the array 190 can be disposed on the substrate 192 or directly on the second major surface 132 of the substrate 130. Each of the detectors of the array 190 can be the same; alternatively, at least one detector of the array can be different from another detector of the array. For example, the first detector 194 can be adapted to detect light having a first wavelength, and the second detector 196 can be adapted to detect light having a second wavelength that is the same as or different from the first wavelength. In one or more embodiments, the detectors of the detector array 190 can be independently addressable such that one or more of the detectors can be turned on or off independent from one or more additional detectors of the array.

Returning to FIGS. 1-5, the electronic device 40 can be electrically connected to one or more additional electronic devices disposed on one or both of the first major surface 32 and second major surface 34, or within the housing 20. For example, the electronic devices 40 can be electrically connected to the power source 50 using any suitable technique or techniques. In one or more embodiments, the electronic devices 40 can include one or more device contacts 44 (FIG. 3) that are electrically connected to one or more of the electronic devices using any suitable technique or techniques. Device contacts 44 are electrically connected to one or more devices 40 through conductors 46. Although illustrated as including two device contacts 44, the package 10 can include any suitable number of device contacts. The device contacts 44 can include any suitable contacts, pads, terminals, etc., that provide electrical connection to other devices, e.g., power source 50. The contacts 44 can take any suitable shape or combination of shapes and be disposed in any suitable location on or in the first major surface 32 of the substrate 30. Any suitable technique or techniques can be utilized to form device contacts 44 and conductors 46, e.g., chemical vapor deposition, plasma vapor deposition, physical vapor deposition, etc., followed by photolithography, chemical etching, etc. Further, the device contacts 44 and conductors 46 can include any suitable conductive material or combination of conductive materials. In one or more embodiments, the electronic devices 40 can be electrically connected to other electronic circuitry or devices disposed on or adjacent the substrate 30 or within the housing 20.

The electronic devices 40 can be electrically connected to device contacts 44 and conductors 46, 82, 92 using any suitable technique or techniques. For example, in one or more embodiments, solder bumps and/or contact pads of the electronic devices 40 can be directly attached to one or more contacts 44 using any suitable technique or combination of techniques, e.g., soldering, welding, laser bonding, mechanically connecting (e.g., direct-pressure contacts), etc. In one or more embodiments, one or more conductors 46, 82, 92 can be electrically connected to one or more device contacts 44 and one or more solder bumps and/or contact pads of one or more of the electronic devices 40 using any suitable technique or combination of techniques, e.g., soldering, welding, laser bonding, mechanically connecting (e.g., direct-pressure contacts), etc.

Any suitable technique or techniques can be utilized to dispose the device contacts 44 and the conductors 46, 82, 92 on the substrate 30, e.g., the techniques described in U.S. Patent Publication No. 2016/0185081, entitled KINETICALLY LIMITED NANO-SCALE DIFFUSION BOND STRUCTURES AND METHODS. For example, electromagnetic radiation can be directed through substrate 30 from the second major surface 34 to a region between the device contacts 44 and the substrate 30, and between the conductors 46, 82, 92, and the substrate 30. The electromagnetic radiation can form a bond that seals the device contacts 44 and the conductors 46, 82, 92 to the substrate 30 in any suitable pattern or shape. The bond can be a laser bond.

The package 10 can also include power source 50. Any suitable power source or combination of power sources can be utilized with package 10, e.g., one or more batteries, capacitors, inductive-coupled energy devices, photovoltaic devices, betavoltaic devices, alphavoltaic devices, and thermo-electric devices.

The power source 50 can be disposed in any suitable location. In one or more embodiments, the power source 50 is disposed at least partially within the housing 20. As used herein, the term "at least partially within" means that at least a portion of the power source 50 is disposed within the housing 20. In one or more embodiments, the entire power source 50 can be disposed within the housing 20. The power source 50 can include its own housing or casing. In one or more embodiments, the housing 20 provides at least a portion of an outer casing for the power source 50. For example, the inner surface 22 of the housing 20 can provide a portion of a casing of the power source 50, and a separate cover or protective layer can be disposed within the housing such that the power source is between the protective layer and the inner surface of the housing. The power source 50 can be integral with the housing 20. In one or more embodiments, the power source 50 is a separate element that is separately manufactured and then disposed within the housing 20.

The power source 50 includes one or more power source contacts 52, 54. Although depicted as including three contacts 52, 54 the power source 50 can include any suitable number of contacts that can be electrically connected to one or more devices to provide electrical energy to such devices from the power source. The power source contacts 52, 54 can be disposed in any suitable location relative to the power source 50. As illustrated in FIG. 2, the power source contacts 52, 54 are disposed at a first end 53 of the power source 50.

The power source contacts 52, 54 can include any suitable contact, e.g., the same contacts described regarding device contacts 44. In one or more embodiments, the power source contacts 52, 54 can include one or more compressible or resilient members that can engage one or more device contacts, e.g., device contacts 44, when the substrate 30 is sealed to the housing 20. Each power source contact 52, 54 can be the same contact or type of contact. In one or more embodiments, each power source contact 52, 54 can be different from each additional power source contact.

The electronic devices 40 can, in one or more embodiments, be electrically connected to the power source 50 using any suitable technique or techniques. In one or more embodiments, the one or more of the electronic devices 40 can be electrically connected to the power source 50 when the substrate 30 is sealed to the housing 20. Any suitable technique or techniques can be utilized to electrically connect the electronic devices 40 to the power source 50 when the substrate 30 is sealed to the housing 20. For example, one or more power source contacts 52, 54 can be electrically connected to one or more device contacts 44 when the substrate 30 is sealed to the housing 20. Any suitable electrical coupling between the power source contacts 52, 54 and the device contacts 44 can be utilized. In one or more embodiments, a non-bonded electrical connection can be formed between one or more device contacts 44 and one or more power source contacts 52, 54 when the substrate 30 is sealed to the housing 20. As used herein, the term "non-bonded electrical connection" means that an electrical connection is formed between two or more contacts, terminals, electrodes, etc., that can be maintained by suitable contact pressure between the two or more contacts to maintain the electrical connection, without the use of a bonding agent, e.g., a conductive adhesive, solder, etc. In one or more embodiments, a bonded electrical connection can be formed between one or more device contacts 44 and one or more power source contacts 52, 54 using any suitable technique or combination of techniques.

The substrate 30 can be sealed to the housing 20 using any suitable technique or techniques, e.g., mechanically fastening, adhering, press fitting, laser bonding, magnetic coupling, etc. In one or more embodiments, the first major surface 32 of the substrate 30 can be sealed to an edge surface 29 of a flange 28. The flange 28 can be integral with the housing 20. In one or more embodiments, the flange 28 can be attached to the housing using any suitable technique or techniques.

In one or more embodiments, the substrate 30 can be hermetically sealed to the housing 20. Any suitable technique or techniques can be utilized to hermetically seal the substrate 30 to the housing 20. For example, in one or more embodiments, the substrate 30 can be hermetically sealed to the housing 20 by a bond. Any suitable technique or techniques can be utilized to form such bond, e.g., the techniques described in co-owned and co-filed U.S. Patent Publication No. 2016/0185081, entitled KINETICALLY LIMITED NANO-SCALE DIFFUSION BOND STRUCTURES AND METHODS. In one or more embodiments, electromagnetic radiation (e.g., light) can be directed through substrate 30 from the second major surface 34 and focused at a region between the substrate and the housing 20. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 2000 nm. For example, laser light can include UV light, visible light, IR light, and combinations thereof. The UV light can be provided by a UV laser that has any suitable wavelength or range of wavelengths and any suitable pulse width. In one or more embodiments, a UV laser can be utilized to provide light having a wavelength in a range of 100-400 nm and a pulse width in a range of 1-100 ns. In one or more embodiments, the materials for the substrate 30 and the housing 20, and the power level and wavelength of the light used may be selected such that the light may not directly damage, ablate, warp, or cut the substrate and the housing, and such that the substrate and the housing retain their bulk properties.

In general, light can be provided by any suitable laser or laser system. For example, the laser may generate light having a relatively narrow set of wavelengths (e.g., a single wavelength). In one or more embodiments, the light emitted by the laser may form a collimated beam that may not be focused at a particular point. In one or more embodiments, the light emitted by the laser may be focused at a focal point at a region between the first major surface 32 of the substrate 30 and the housing 20 to generate a laser bond.

Although the laser may provide light that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat, Gaussian, or other suitable spatial energy profile.

As mentioned herein, one or more electronic devices 40 can be disposed on the first major surface 32 of the substrate 30. In one or more embodiments, one or more additional devices or features can also be disposed on the second major surface 34 of the substrate 30. For example, in the embodiment illustrated in FIGS. 1-5, the first electrode 74 and the second electrode 76 are disposed on the second major surface 34 of the substrate 30. The first and second electrodes 74, 76 can include any suitable electrode or combination of electrodes and can take any suitable shape and have any suitable dimensions.

One or both of the first and second electrodes 74, 76 can be utilized to electrically connect the package 10 to any suitable device or devices that are external to the package. For example, one or both of the first and second electrodes 74, 76 can electrically connect the package 10 to a lead of an implantable medical device. In one or more embodiments, one or both of the first and second electrodes 74, 76 can electrically connect the package 10 to one or more additional power sources. Further, in one or more embodiments, one or both of the first and second electrodes 74, 76 can be therapeutic electrodes that can be utilized for delivering and/or receiving one or more electrical signals to or from a patient, either while the package is external or internal to a patient. Any suitable technique or techniques can be utilized to electrically connect the package 10 to one or more devices through one or both of the first electrode 74 and second electrode 76, e.g., soldering, physical contact, welding, etc. The first and second electrodes 74, 76 can include any suitable conductive material or combination of conductive materials, e.g., copper, silver, titanium, niobium, zirconium, tantalum, stainless steel, platinum, iridium, or combinations thereof. In one or more embodiments, the first and second electrodes 74, 76 can include two or more materials, e.g., bi-metals, clad laminates, etc.

Further, the first and second electrodes 74, 76 can take any suitable shape or combination of shapes. In one or more embodiments, the first and second electrodes 74, 76 can take a circular shape in a plane parallel to the second major surface 34 of the substrate 30. In one or more embodiments, the first and second electrodes 74, 76 can take a rectangular shape in the plane parallel to the second major surface 34. Further, the first and second electrodes 74, 76 can take any suitable shape or combination of shapes in a plane orthogonal to the second major surface 34, e.g., square, tapered, domed, etc. In one or more embodiments, the first and second electrodes 74, 76 can include complex shapes such as grooves or channels formed in the electrode to facilitate attachment of conductors or electronic devices to the contacts.

The first and second electrodes 74, 76 can also include any suitable dimensions. In one or more embodiments, the first and second electrodes 74, 76 can have any suitable thickness in a direction normal to the second major surface 34 of the substrate 30. In one or more embodiments, this thickness can be at least 10 micrometers. In one or more embodiments, the thickness can be no greater 200 micrometers. In one or more embodiments, the first and second electrodes 74, 76 can be of sufficient size and thickness to enable laser, resistance, or other welding and joining techniques to be utilized to electrically couple conductors and/or electronic devices to the electrode.

The first and second electrodes 74, 76 can be electrically connected to one or more electronic devices disposed on or within the package, e.g., electronic device 40. Any suitable technique or techniques can be utilized to electrically connect one or both of the first and second electrodes 74, 76 to one or more devices disposed on or within the housing. In one or more embodiments, the first electrode 74 can be electrically connected to device 40 through via 78 (FIG. 3), which is electrically connected to device 40 through conductor 75. Via 78 can be formed between the first major surface 32 and the second major surface 34 of the substrate 30, and a conductive material can be disposed within the via using any suitable technique or combination of techniques. Similarly, second electrode 76 can be electrically connected to electronic device 40 through via 79 (FIG. 3), which is electrically connected to the device through conductor 77. Once again, via 79 can be formed between the first major surface 32 and the second major surface 34 of substrate 30, and conductive material can be disposed within the via using any suitable technique or combination of techniques.

The package 10 of FIGS. 1-5 can also include the conductor 70 disposed on the second major surface 34 of the substrate 30 or within the substrate between the first major surface 32 and the second major surface 34. The conductor 70 can include any suitable shape or combination of shapes and can be formed using any suitable conductive material. Although depicted as including one conductor 70, two or more conductors can be formed on the second major surface 34 of the substrate 30 or within the substrate. Further, the conductor 70 can be patterned to include any suitable shape or combination of shapes.

In one or more embodiments, the conductor 70 can be formed to provide an antenna, and the package 10 can be wirelessly coupled to a device or system through such antenna. The package 10 can wirelessly communicate through the antenna utilizing, e.g., RF, inductive, optical, magnetic, acoustic, or other transmission mechanisms. Further, in one more embodiments, the conductor 70 can form an inductive coil that can be utilized to provide inductive coupling to one or more external devices, e.g., one or more inductive power sources.

The conductor 70 can be electrically connected to one or more electronic devices disposed within the housing of the package 10 using any suitable technique or techniques. For example, a via (not shown) can be formed between the first major surface 32 and the second major surface 34 of the substrate 30 that is that is electrically connected to, e.g., one or more electronic devices 40 through a conductor. Conductive material can be disposed within the via that electrically connects the conductor 70 to one or more electronic devices 40. The conductor 70 can be electrically connected to the via using any suitable technique or techniques.

The electronic devices 40 can include an accelerometer (not shown) disposed in any suitable location on or within the substrate 30 or housing 20 of the package 10. In one or more embodiments, the accelerometer can be utilized to mitigate potentially confounding influences caused by the motion and/or posture of the patient. A measurement period of the package 10 can be deferred if the accelerometer or other electronic device 40 detects a high activity level of the patient until such time that a low activity level occurs. In one or more embodiments, a measurement period can be deferred until the patient is in a preferred posture.

Likewise, for ambient light, the detector 90 can detect an ambient light level. If the ambient light level is below a selected low level threshold, then measurement of a physiological condition of the patient can proceed. If the level is above the low-level threshold but below an intermediate ambient light threshold, then physiological measurements may proceed. The controller 42 can be adapted to subtract or remove the ambient light level from the measurement. If the ambient light level is above a high ambient light threshold, then the measurement can be deferred until ambient light returns to a level below the intermediate or low ambient light thresholds. The controller 42 can also be adapted to defer measurement based upon other conditions, e.g., temperature, respiration, ECG anomalies, etc. Deferring measurement based upon one or more selected conditions can help to preserve battery power and to capture physiologically meaningful data, e.g., measurement may be activated when a patient is having an ECG episode.

The various embodiments of packages described herein can be utilized to determine one or more physiological conditions. Any suitable physiological condition can be determined, e.g., heart rate, arterial blood oxygen level ($SpO_2$), blood flow, fluid volume (e.g., edema), tissue oxygen saturation ($StO_2$), perfusion index (PI), Total Hemoglobin/Hematocrit, Tissue Hemoglobin Concentration Index (THI), venous oxygen saturation ($SvO_2$), ambient light level within a patient, respiration rate, optically interrogated biochemical sensors (e.g., fluorescent or other coatings and materials in contact with tissue), pulse wave velocity (e.g., pulse transit time), etc.

Figure 7:
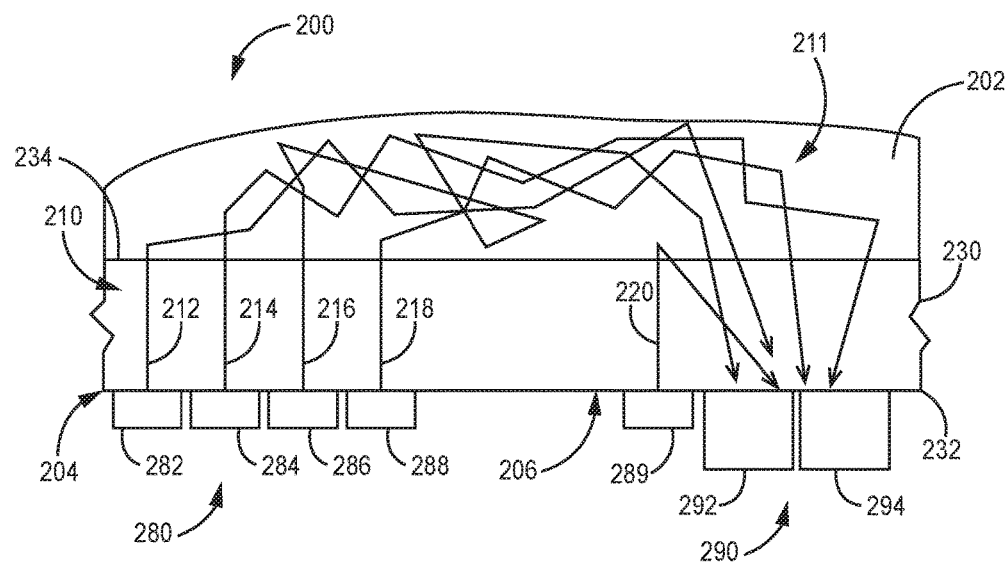
FIG. 7 is a schematic cross-section view of another embodiment of a sealed package disposed within a patient and adjacent tissue of the patient.

For example, FIG. 7 is a schematic cross-section view of a portion of one embodiment of a sealed package 200 implanted within a patient adjacent or within tissue 202. All of the design considerations and possibilities regarding the package 10 of FIGS. 1-5 apply equally to the package 200 of FIG. 7. The package 200 includes a housing (not shown for clarity) and a substrate 230 sealed to the housing. Light source array 280 is disposed on a first portion 204 of a first major surface 232 of the substrate 230 and includes a first light source 282, a second light source 284, a third light source 286 and a fourth light source 288. The light source array 280 further includes a fifth light source 289 disposed on a second portion 206 of the first major surface 232 of the substrate 230. Each of the light sources of the array 280 is adapted to emit light 210 through the first major surface 232 and a second major surface 234 of the substrate 230.

The package 200 also includes a detector array 290 that includes a first detector 292 and a second detector 294 each disposed on the first major surface 232 of the substrate 230. Each detector of the detector array 290 is adapted to detect at least a portion of the light 210 emitted by the light source array 280.

Light 210 emitted from the light source array 280 is scattered and absorbed by the body fluid or tissue volume 202. At least a portion of light 211 that is scattered by the volume 202 travels through the substrate 230 to the detector array 290. Scattered light that corresponds to wavelengths to which the detector array 290 is responsive will cause one or both of the detectors 292, 294 to generate current or voltage corresponding to various characteristics (e.g., intensity) of the detected light. Light modulation due to a physiological change may result in a signal generated by the detector array 290 that may be correlated to a changing physiological condition.

Each light source of the light source array 280 can be adapted to emit light having a selected characteristic. For example, light source 282 can be adapted to emit light 212 having a first wavelength, light source 284 can be adapted to emit light 214 having a second wavelength, light source 286 can be adapted to emit light 216 having a third wavelength, and light source 286 can be adapted to emit light 218 having a fourth wavelength. Further, light source 289 can be adapted to emit light 220 having a fifth wavelength. The light emitted by each of the light sources of the array 280 can have the same wavelength or different wavelengths as the light emitted by one or more of the other light sources of the array.

Similarly, the various detectors of the detector array 290 can each be adapted to detect light having a selected characteristic (e.g., wavelength). For example, detector 292 can be adapted to detect light 212, 218, and 220 that has been emitted by light sources 282, 288, and 289 and scattered by volume 202. Further, detector 294 can be adapted to detector light 214 and 216 emitted by light sources 284 and 286.

As such, light scattered by body fluid or tissue volume 202 can cause the detector array 290 responsive to selected light wavelengths to emit a signal useful in measurement of one or more physiological conditions (or changes in such physiological conditions) in the body fluid or tissue volume. For example, the light source array 280 and detector array 290 can be adapted to estimate oxygen saturation in blood. In such an embodiment, one or more light sources of the light source array 280 can be adapted to emit red light. The intensity of red light scattered by the body fluid or tissue volume 202 and detected by detector array 290 is dependent on the concentration of oxygenated hemoglobin in the blood. The intensity of infrared light scattered by the body fluid or tissue volume 202 can be made independent of the concentration of oxygenated hemoglobin by proper choice of wavelength (e.g., 800 nm). The scattered red light detected can be normalized by the infrared light detected to correct for variables such as total hemoglobin, tissue overgrowth, and blood flow velocity or other artifacts.

Figure 8:
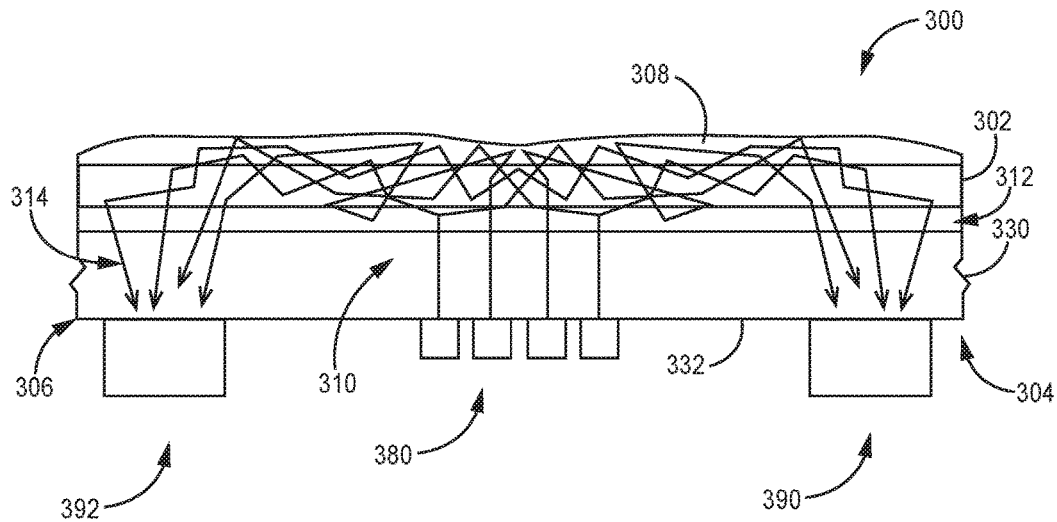
FIG. 8 is a schematic cross-section view of another embodiment of a sealed package disposed within a patient and adjacent an artery of the patient.

In one or more embodiments, a sealed package described herein can measure pulse wave velocity of blood flow of a patient. For example, FIG. 8 is a schematic cross-section view of a portion of another embodiment of a sealed package 300 implanted within a patient adjacent an artery 302. All of the design considerations and possibilities regarding the sealed package 10 of FIGS. 1-5 apply equally to the sealed package 300 of FIG. 8. The package 300 includes a housing (not shown for sake of clarity) and a substrate 330 sealed to the housing. The package 300 also includes a light source array 380 disposed on a first major surface 332 of the substrate 330. The package 300 further includes a first detector 390 disposed on a first portion 304 of the first major surface 332 of the substrate 330, and a second detector 392 disposed on a second portion 306 of the first major surface of the substrate.

The light source array 380 can be adapted to emit light of any suitable wavelength or wavelengths. In one or more embodiments, each light source of the array 380 can emit the same wavelength as one or more additional light sources or different wavelengths. Further, the detectors 390, 392 can be adapted to detect any suitable wavelength or wavelengths.

In general, the package 300 can be disposed adjacent or in contact with the artery 302 such that at least a portion of light 310 emitted by one or more of the light sources 380 is incident upon the artery. A first portion 312 of the emitted light 310 is incident upon the artery 302 and is scattered by the artery and surrounding tissue 308. At least a portion of the first portion 312 of light is incident upon the first detector 390, which detects the portion and sends a first signal to a controller or other electronic device (e.g., controller 42 of FIG. 1) disposed within the housing of the package 300. Further, a second portion 314 of light is emitted by the light sources 380 and incident upon the artery 302, where it is scattered by the artery and surrounding tissue 308. At least a portion of the second portion 314 of light is incident upon the second detector 392, which detects the portion of light and sends a second signal to the controller.

Any suitable technique can be utilized to determine the pulse wave velocity of blood flowing through the artery 302 based upon the first signal and second signal. For example, ECG and single pulsatile optical signal (photoplethysmography PPG) can be simultaneously measured in time sync. The R wave from the ECG signal can be detected and marked. A fiducial on the PPG such as peak amplitude or initial onset of the systolic response can also be marked. The time interval between the occurrence of the R wave and the PPG fiducial can be measured to determine a pulse transit time. The pulse wave velocity can be calculated based upon the pulse transit time using any suitable technique or techniques.

Further, for example, pulse velocity may be derived by measuring the time between two PPG events utilizing two or more sensors disposed in different positions within the package 300. A fiducial can be applied to each wave form. And the time delay between the two wave forms can be measured to determine pulse velocity.

Figure 9:
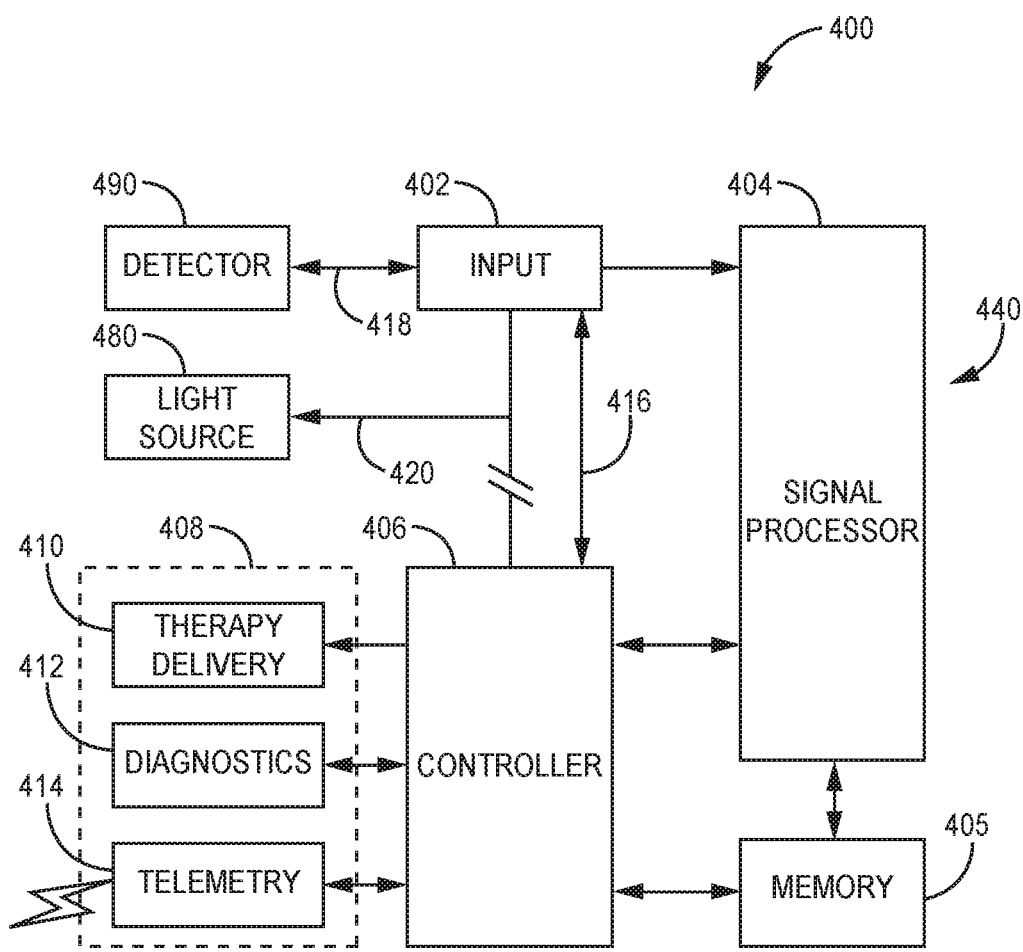
FIG. 9 is a schematic diagram of another embodiment of a sealed package.

Any suitable circuitry or components can be utilized with the various embodiments of sealed packages described herein to provide information regarding a physiological condition or conditions of a patient. For example, FIG. 9 is a schematic block diagram of one embodiment of another embodiment of a sealed package 400. All of the design considerations and possibilities regarding the sealed package 10 of FIGS. 1-5 apply equally to the sealed package 400 FIG. 9. The package 400 includes a housing and a substrate (neither shown for sake of clarity). The package 400 also includes a light source 480 and a detector 490 each disposed on a first major surface of the substrate as is further described herein.

Sealed package 400 can include one or more electronic devices 440 (including the light source 480 and the detector 490) disposed on one or both of a first major surface and a second major surface of the substrate or within the housing (e.g., electronic devices 40 of FIGS. 1-5). In addition to the light source 480 and the detector 490, the electronic devices 440 include an input module 402, signal processor 404, memory 405, controller 406, and output module 408.

Input module 402 receives one or more signals when enabled for sensing by controller 406 by control/status line 416. Input module 402 may perform pre-processing signal conditioning, such as analog filtering. Input module 402 selects the functionality of the light source 480 and the detector 490 via control bus 418 and 420 under the control of controller 406. Input module 402 further provides one or more signals from detector 490 to signal processor 404. Input module 402 may additionally provide other sensor signals to processor 404 and/or controller 406 for use in monitoring physiological signals and detecting physiological conditions or events.

The techniques employed for controlling the light source 480 and the detector 490 will depend in part on the overall medical device architecture and hardware, firmware, and software employed. In one or more embodiments where the light source 480 includes multiple light sources and the detector 490 includes multiple detectors, selection of a light source and detector to operate includes providing a control signal on control bus 418 for coupling the detector 490 to a photo-integrator that converts the device-generated current to a voltage signal, which is then provided to an A/D converter. Selection of a light source 480 generally includes coupling the source to a drive signal source to activate the light source to emit light. One example of a bus system for controlling a device is generally disclosed in U.S. Pat. No. 7,013,178 (Reinke, et al.).

Processor 404 receives the signals from the detector 490 and performs signal processing to provide controller 406 with signals useful in monitoring a patient condition and appropriately control output module 408. Processor 404 may be a digital signal processor (DSP), analog processor, or a combination of both analog and digital processors.

Controller 406 controls input module 402 to select the functionality of the light source 480 and detector 490 during a performance test. The sealed package 400 can execute an optical sensor performance test to evaluate optical sensor signals obtained during different assembly functionality configurations. The functional configuration of the light source 480 and the detector 490 are controlled by the controller 406. The controller 406 controls the selection of each assembly to function as either a light emitting portion or a light detecting portion (or neither or both light emitting and light detecting in some embodiments) in a functional configuration of the light source 480 and detector 490 used for patient monitoring.

During a performance test, functionality of the light source 480 and detector 490 are controlled and detector signals are provided to processor 404. Processor 404 provides the controller 406 signal data from which controller 406 determines the optimal assembly functionality configuration for optical sensing. The optimal sensing configuration is then selected by input module 402 under the control of controller 406 during episodes in which the light source 480 and detector 490 are enabled for monitoring physiological signals.

Signal data may be stored in memory 405 by processor 404 and retrieved by controller 406 for use in determining an optimal functional configuration of the light source 480 and detector 490. Algorithms for a performance test and other functions may also be stored in memory 405 and retrieved by controller 406.

During normal operation, controller 406 analyzes processed signals provided by processor 404 to detect physiological events or patient conditions. Controller 406 can determine which emitting and detecting configurations of the light source 480 and detector 490 provide signals with the highest signal-to-noise ratio and acceptable signal level and may select additional light sources, detectors, and other types of sensors (e.g., an accelerometer) to operate to provide redundant signals to promote accurate detection. In one or more embodiments, controller 406 may select emitting and detecting configurations of one or both of the light source 480 and sensor 490 that minimize energy demands while providing a reliable sensor signal for use in patient monitoring. The ability to select the functionality of one or both of the light source 480 and sensor 490 over time allows the sealed package 400 to accommodate situations in which signal characteristics change over time, for example, due to shifting of the package or changes in adjacent tissue composition such as increased tissue encapsulation. By periodically repeating performance tests, controller 406 can select the optimal configuration light sources and detectors as it changes over time.

Controller 406 uses the digitally processed signals to make decisions regarding therapy delivery by therapy delivery module 410, for determining and storing a diagnostic output (such as a detected physiological event) in diagnostics module 412, and/or for selecting data to be transmitted by telemetry module 414. Controller 406 may employ a microprocessor and associated memory 405 or digital state machines for timing sensing and therapy delivery functions and controlling other device operations in accordance with a programmed operating mode. The signal acquisition, processing and analysis methods described herein and selection of one or more light sources and detectors may be implemented using any combination of software, hardware, and/or firmware.

Therapy delivery module 410 may provide electrical stimulation therapy or drug delivery therapy. In one or more embodiments, therapy delivery module 410 includes a pulse generator for generating low-voltage pacing pulses, e.g., for bradycardia pacing, cardiac resynchronization therapy, and anti-tachycardia pacing. Therapy delivery module 410 may further include high-voltage circuitry for generating high-voltage cardioversion/defibrillation shocks. Therapy delivery unit 410 includes therapy delivery elements (not explicitly shown) such as electrodes, catheters, drug delivery ports or the like for administering a therapy.

Diagnostics module 412 may be used to detect a physiological event or patient condition using any available sensor signals or other data acquired by the IMD and store data relating to the analysis of processed signals. Stored data may be made available to a clinician through telemetry by telemetry module 414 or accessed by controller 406 for making therapy decisions.

The controller 406 can be adapted to control the light source 480 and detector 490 in any suitable manner to detect any desired physiological condition or characteristic of a patient as is described in co-owned and co-filed U.S. patent application Ser. No. 15/477,835, entitled HERMETICALLY-SEALED PACKAGE AND METHOD OF FORMING SAME (the '400 Application).

Further, the sealed packages described herein can be manufactured using any suitable technique or techniques, e.g., the techniques described in co-owned U.S. Patent Application No. 62/250,194, filed Nov. 3, 2015, and entitled SEALED PACKAGE INCLUDING ELECTRONIC DEVICE AND POWER SOURCE, and the '400 Application. Further, the various embodiments of sealed packages described herein can be utilized with any technique or techniques to determine a characteristic or physiological condition of a patient, e.g., the techniques described in the '400 Application.

One or more embodiments of packages described herein can include one or more optical devices or elements that are adapted to redirect or absorb light that is emitted by a light source of the package and propagates along a light guide of the package. Further, such optical devices can also be adapted to redirect or absorb emitted light that has been scattered by tissue of a patient and directed into the substrate where it propagates along the substrate. By redirecting or absorbing this light, the optical devices can improve a signal-to-noise ratio of the detector, thereby improving sensitivity of the package. Further, such optical devices can utilize any suitable optical technique or techniques to redirect or absorb light, e.g., reflection, refraction, scattering, absorption, etc.

Figure 10:
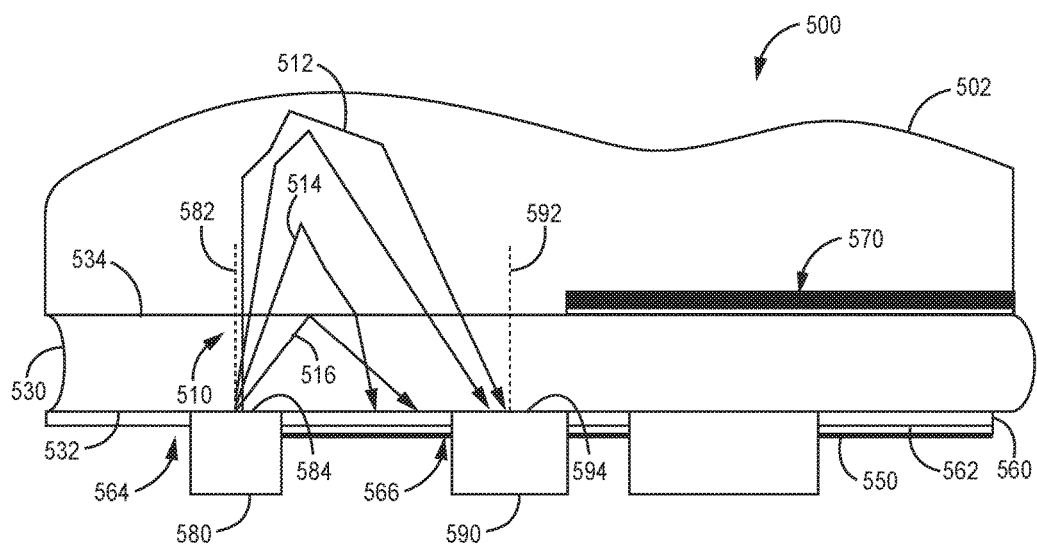
FIG. 10 is a schematic cross-section view of another embodiment of a sealed package disposed within a patient and adjacent tissue of the patient.

FIG. 10 is a schematic cross-section view of another embodiment of a sealed package 500. All of the design considerations and possibilities regarding the sealed package 10 of FIGS. 1-5 apply equally to the package 500 of FIG. 10. The package 500 includes a housing (not shown for clarity) and a substrate 530 sealed to the housing. The package 500 also includes a light source 580 disposed on a first major surface 532 of the substrate 500, where the light source includes an emitting surface 584. The package 500 also includes a detector 590 disposed on the first major surface 532 of the substrate 530, where the detector includes a detecting surface 594. In one or more embodiments, the package 500 can also include an antenna 570 disposed on a second major surface 534 of the substrate 530.

One difference between package 500 and package 10 is that a masking layer 560 is disposed on the first major surface 532 of the substrate 530. In one or more embodiments, the masking layer 560 can be disposed on the second major surface 534 of the substrate 530. Further, in one or more embodiments, the masking layer 560 can be disposed on the first major surface 532 of the substrate 530, and a second masking layer can be disposed on the second major surface 534.

In one or more embodiments, the masking layer 560 can be adapted to redirect or absorb light 510 emitted by the light source 580 that propagates within the substrate 530 before such light is incident upon the detecting surface 594 of the detector 590. For example, light 516 is emitted by the light source 580 and is totally internally reflected at a boundary between the light guide 530 and surrounding tissue 502 or bodily fluid. The light 516, therefore, propagates within the substrate 530. Such light 516, however, is redirected or absorbed by the masking layer 560 before it reaches the detecting surface 594 of the detector 590. Further, light 514 is emitted by the light source 580 and is incident upon tissue 502, where it is scattered by the tissue and directed into the light guide 530. This light 514 is incident upon the masking layer 560 and is redirected or absorbed before it can reach the detecting surface 594 of the detector 590. Further, light 512 is emitted by the light source 580 and is incident on the tissue 502, where it is scattered and directed to the detecting surface 594 of the detector 590. Such scattered light 512 can provide a detector signal that is representative of the physiological characteristic or characteristics that are desirably detected. In one or more embodiments, the use of the masking layer 560 can help optimize a signal level and dynamic range of the detector 590 by redirecting or absorbing unwanted light, i.e., light that is not representative of the physiological characteristic to be detected.

The masking layer 560 can include any suitable number of layers. Further, the masking layer 560 can include any suitable material or materials, e.g., polymeric, metallic, inorganic materials, and combinations thereof. In one or more embodiments, the masking layer 560 can include a dielectric material. In one or more embodiments, the masking layer 560 can include an electrically conductive material. In one or more embodiments, the masking layer 560 can include a light absorbing material such that the layer is adapted to absorb light having any suitable wavelength or range of wavelengths, e.g., one or more of ultraviolet, visible, near infrared, and infrared light. Suitable materials for the masking layer 560 include TiN, fractal TiN, titanium, etc.

If the masking layer 560 includes electrically conductive materials, then an optional insulating layer 562 can be disposed between the masking layer and one or more conductors 550. The insulating layer 562 can include any suitable material or materials that insulate the masking layer 560 from the conductor 550, e.g., siloxane, silicon nitride, etc. In one or more embodiments, the insulating layer 562 includes a dielectric material.

The masking layer 560 can be disposed on any suitable portion or portions of the first major surface 532 of the substrate 530 using any suitable technique or techniques. In one or more embodiments, the masking layer 560 can be disposed on the first major surface 532 using, e.g., plasma vapor deposition, chemical vapor deposition, plasma vapor deposition, physical vapor deposition, etc., followed by photolithography, chemical etching, etc.

Further, the masking layer 560 can be disposed in any suitable pattern or patterns. For example, in the embodiment illustrated in FIG. 10, the masking layer 560 includes a first aperture 564 aligned with an emission axis 582 of the light source 580 in a direction orthogonal to the first major surface 532 of the substrate 530. Further, the masking layer 560 also includes a second aperture 566 that is aligned with a detection axis 592 of the detector 590 in the direction orthogonal to the first major surface 532 of the substrate 530. In embodiments where the masking layer 560 is disposed on the first major surface 532 of the substrate 500, the light source 580 can be disposed within the first aperture 564 and the detector 590 can be disposed within the second aperture 566. The first and second apertures 564, 566 allow light 510 emitted by the light source 580 to be directed through the first aperture and the substrate 530 such that it is incident upon the tissue 502. Such light 512 can be scattered by the tissue 502 and returned to the detector 590 through the second aperture 566.

Each of the first and second aperture is 564, 566 can take any suitable shape or combination of shapes. In one or more embodiments, the masking layer 560 can be disposed such that the light source 580 is lateral to an edge of the masking layer in a direction parallel to the first major surface 532 of the substrate 530. Further, in one or more embodiments, one or both of the first and second apertures 564, 566 can be a slot such that one or both of an array of light sources 580 and an array of detectors 590 can be disposed within the same aperture. For example, in one or more embodiments, the second aperture 566 can take an elongated slot shape such that two or more detectors 590 can be disposed within the aperture, i.e., the detection axis of each of the detectors is aligned within the second aperture in the direction orthogonal to the first major surface 532 of the substrate 530.

Figure 11:
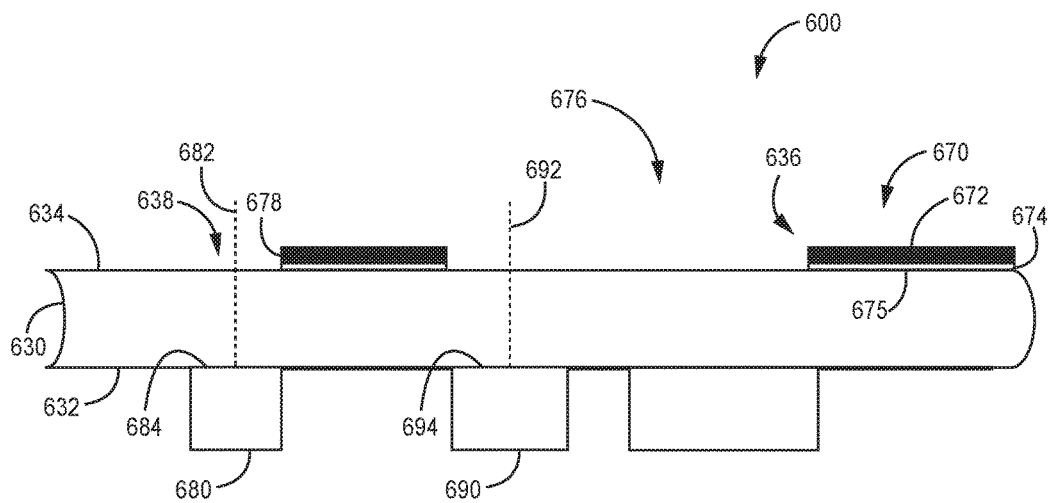
FIG. 11 is a schematic cross-section view of another embodiment of a sealed package.

As mentioned herein, any suitable optical device or element can be utilized to redirect or absorb unwanted light that is emitted by the light source. For example, FIG. 11 is a schematic cross-section view of another embodiment of a package 600. All of the design considerations and possibilities regarding the package 10 of FIGS. 1-5 and the package 500 of FIG. 10 apply equally to the package 600 of FIG. 11.

The package 600 includes a light source 680 having an emission axis 682. The light source 680 is disposed on a first major surface 632 of substrate 630. The package 600 also includes an antenna 670 disposed on a second major surface 634 of the substrate 630. In one or more embodiments, the antenna 670 is disposed on a first portion 636 of the second major surface 634 of the substrate 630. The light source 680 can be disposed such that the emission axis 682 is aligned with a second portion 638 of the second major surface 634 of the substrate 630 in a direction orthogonal to the first major surface 632 of the substrate such that the light source is disposed laterally from an outside edge 678 of the antenna. Further, the antenna 670 includes a first interstitial portion 676. As used herein, the term "interstitial" refers to a portion or portions of the antenna 670 that are formed as openings or spaces within an outer boundary formed by an outer edge of the antenna. The detector 690 is aligned with the first interstitial portion 676 in a direction orthogonal to the first major surface 632 of the substrate 630. In other words, a detection axis 692 of the detector 690 is aligned within the interstitial portion 676 of the antenna 670 in a direction orthogonal to the first major surface 632 of the substrate 630.

Light emitted by the light source 680 and scattered by tissue of a patient such that it would be incident upon the light guide 630 in portions where the light would not reach the detector 690 can be reflected by the antenna 670, thereby only allowing scattered light that will be incident upon a detecting surface 694 of the detector 690 on a first pass through the substrate 630 to reach the detector.

In one or more embodiments, the antenna 670 can include a conductive layer 672 and a seed layer 674 disposed between the conductive layer and the second major surface 634 of the substrate 630. In one or more embodiments, the seed layer 674 can be utilized to form the conductive layer 672 on the substrate 670.

The seed layer 674 can include any suitable material or materials. In one or more embodiments, the seed layer 674 can include a material that absorbs light such that light emitted by the light source 680 that propagates within the substrate 630 can be absorbed by the seed layer prior to being incident upon the detecting surface 694 of the detector 690. The seed layer 674 can, therefore, be a masking layer (e.g., masking layer 560 of FIG. 10) by redirecting or absorbing light that is propagating within the substrate 630.

In one or more embodiments, the seed layer 674 can include a textured or roughened surface 675 at an interface with the substrate 630. Such surface 675 can be roughened using any suitable technique or techniques, e.g., laser texturing, chemical etching, mechanical etching, etc. In one or more embodiments, the roughened surface 675 can be formed by directing laser light through the first major surface 632 of the substrate 630 and onto the seed layer 674. The roughening of the seed layer 674 at the interface with the substrate 630 can increase the light absorption of the seed layer.

Although not shown, the package 600 can also include a masking layer (e.g., masking layer 560 of FIG. 10) disposed on the first major surface 632 of the substrate 630. Such masking layer can also redirect or absorb light that is propagating within the substrate 630 prior to such light entering the detector 690.

Figure 12:
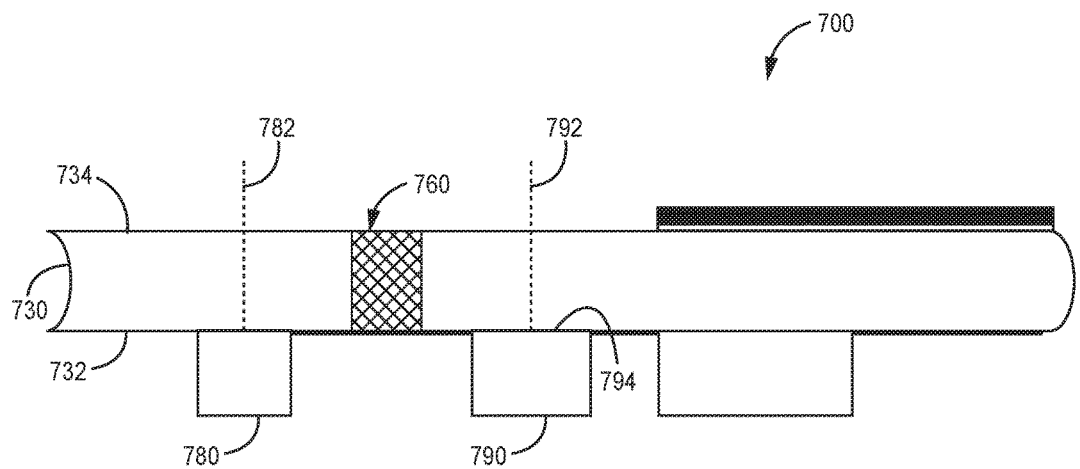
FIG. 12 is a schematic cross-section view of another embodiment of a sealed package.

Various embodiments of packages described herein can include any suitable optical device or element disposed in any suitable location relative to a substrate of the package that can improve a signal of a detector of the package by reducing the amount of unwanted light that reaches the detector. Such optical device or element can be disposed on one or both major surfaces of the substrate or within the substrate. For example, FIG. 12 is a schematic cross-section view of another embodiment of a sealed package 700. All of the design considerations and possibilities regarding the package 10 of FIGS. 1-5 and the package 500 of FIG. 10 apply equally to the package 700 of FIG. 12. One difference between package 700 and package 500 is that a diffuse region 760 is disposed on or in a substrate 730 of the package. In one or more embodiments, the diffuse region 760 includes the same material or materials utilized to form the substrate 730. In one or more embodiments, the diffuse region 760 includes a material or materials that are different from the materials used to form the substrate 730.

The diffuse region 760 can be formed using any suitable technique or techniques. In one or more embodiments, the diffuse region 760 can be formed by altering one or more bulk properties of the substrate 730 using any suitable technique, e.g., laser ablation, chemical etching, etc. For example, in embodiments where the substrate 730 includes sapphire, a femtosecond laser or other suitable laser can be used to treat a bulk of the sapphire substrate and form local regions of amorphous aluminum oxide ($Al_2O_3$). Laser pulses can form either microsized spots of amorphous sapphire within the bulk of the substrate 730 or microvoids at higher power levels of the laser.

Although depicted as including one diffuse region 760, the package 700 can include any suitable number of diffuse regions disposed on or within the substrate 730 in any suitable pattern. In one or more embodiments, an array of diffuse regions 760 can be formed to provide optical barriers within the substrate 730 that can either redirect or absorb light that is propagating within the substrate.

The diffuse region 760 can take any suitable shape or shapes. In one or more embodiments, the diffuse region 760 can extend along a width of the substrate (i.e. in a direction orthogonal to a plane of FIG. 12). Further, the diffuse region 760 can have any suitable depth. In one or more embodiments, the diffuse region 760 can extend between a first major surface 732 and a second major surface 734 of the substrate 730. In one or more embodiments, the diffuse region 760 can have a height as measured in a direction orthogonal to the first and second major surfaces 732, 734 of the substrate 730 that is the same as or less than a height of the substrate 730 measured along the same direction. Further, the diffuse region 760 can have any suitable length as measured in a direction parallel to the first and second major surfaces 732, 734 of the substrate 730 (i.e., in the plane of FIG. 12).

The diffuse region 760 can be disposed in any suitable location on or within the substrate 730. In one or more embodiments, the diffuse region 760 can be disposed between an emission axis 782 of the light source 780 and a detection axis 792 of the detector 790 in a lateral direction parallel to the first major surface 732 of the substrate 730 such that light that propagates within the substrate 730 in a direction toward a detecting surface 794 of the detector can be redirected or absorbed by the diffuse region before reaching the detecting surface.

As mentioned herein, the diffuse region 760 can include a material that is different from the material of the substrate 730. For example, such diffuse region 760 can be formed, e.g., by first forming a void within the substrate 730 and filling the void with a desired material.

In one or more embodiments, the diffuse region 760 can be disposed on one or both of the first and second major surfaces 732, 734 of the substrate 730. Any suitable technique or techniques can be utilized to form such surface diffuse region 760. For example, in one or more embodiments, a laser can be used to shape one or both of the first and major surfaces 732, 734 to provide a diffuse region or regions on one or both major surfaces. Such diffuse surface regions can redirect or absorb light entering one or both of the first and second major surfaces 732, 734 or light that is propagating within the substrate 730. As a result, such diffuse surface region or regions can frustrate total internal reflection of the light that is propagating within the substrate 730 and redirect or absorb the light out of the substrate such that it is incident upon the tissue. The package 700 can include any suitable number of diffuse surface regions 760 disposed in a suitable pattern. Further, the diffuse region 760 can take any suitable shape and have any suitable dimensions on one or both of the first and second major surfaces 732, 734 of the substrate 730.

Figure 13:
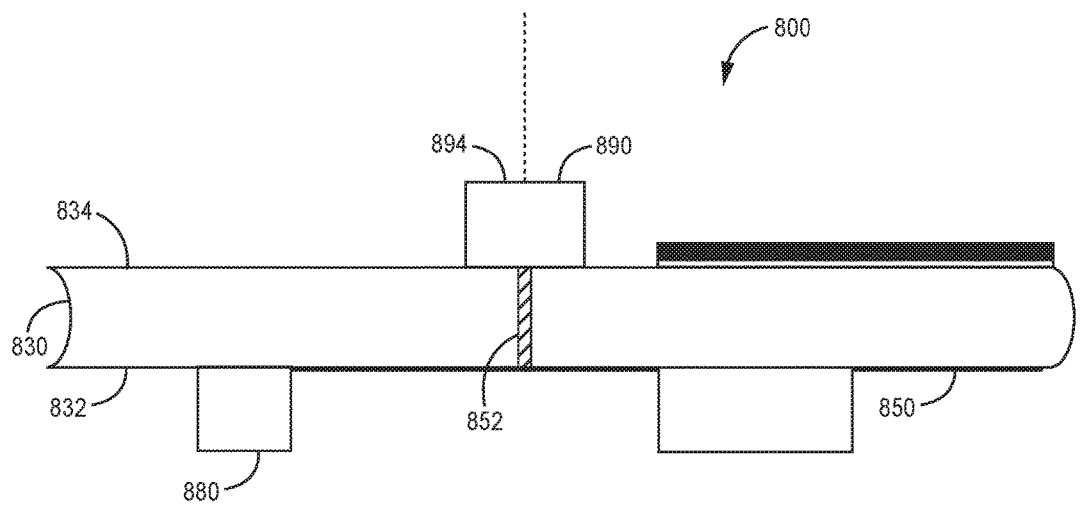
FIG. 13 is a schematic cross-section view of another embodiment of a sealed package.

As mentioned herein, one or more electronic devices can be disposed on a second major surface of a substrate of a sealed package such that the devices are external to a housing of the package. For example, FIG. 13 is a schematic cross-section view of another embodiment of a sealed package 800. All of the design considerations and possibilities regarding the package 10 of FIGS. 1-5 and the package 500 of FIG. 10 apply equally to the package 800 of FIG. 13. The package 800 includes a housing (not shown for clarity), a substrate 830 sealed to the housing and including a first major surface 832 and a second major surface 834, and a light source 880 disposed on the first major surface of the substrate. The package 800 also includes a detector 890 disposed on the second major surface 834 of the substrate 830. In one or more embodiments, the light source 880 can be disposed on the second major surface 834 of the substrate 830 and the detector 890 disposed on the first major surface 832. In one or more embodiments, both the light source 880 and the detector 890 can be disposed on the second major surface 834 of the substrate 830. Further, in one or more embodiments, at least one light source 880 can be disposed on the first major surface 832 and at least one additional light source can be disposed on the second major surface 834. And in one or more embodiments, at least one detector 890 can be disposed on the first major surface 832 and at least one additional detector can be disposed on the second major surface 834.

The package 800 further includes a conductor 850 disposed on the first major surface 832 of the substrate 830. The conductor 850 is electrically connected to a light source 880 disposed on the first major surface 832. A via 852 is disposed between the first major surface 832 and the second major surface 834 of the substrate 830 and is also electrically connected to the conductor 850. The via 852 is further electrically connected to the detector 890.

Any suitable technique or techniques can be utilized to dispose the detector 890 on the second major surface 834 of the substrate 830. In one or more embodiments, the detector 890 can be hermetically sealed to the second major surface 834 over the via 852 using any suitable technique or techniques, e.g., the laser bonding techniques described herein. In one or more embodiments, an encapsulant (not shown) can be disposed over the detector 890 to protect the detector from exposure to body fluids and tissue. Any suitable encapsulant can be utilized, e.g., silicone.

By placing the detector 890 on the second major surface 834 of the substrate 830, light emitted by the light source 880 that propagates within the substrate 830 will not be incident upon a detecting surface 894 of the detector as such surface is not optically coupled to the substrate. Further, the detector 890 can be spaced apart from the light source 880 any suitable distance such that light emitted by the light source that is incident upon tissue of the patient has to travel a greater distance through the tissue before being incident upon the detecting surface 894 of the detector 890.

Figure 14:
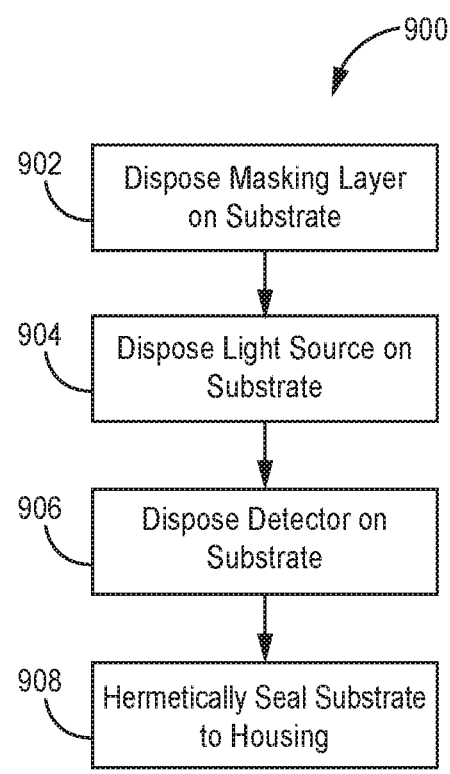
FIG. 14 is a flowchart of another embodiment of a method of forming a sealed package.

Any suitable technique or techniques can be utilized to form the various embodiments of sealed packages described herein that include one or more optical devices. For example, FIG. 14 is a flowchart of one embodiment of a method 900 of forming a hermetically sealed package 500. Although the method 900 will be described in reference to package 500 of FIG. 10, such method can be utilized to form any suitable package.

The method 900 includes disposing the masking layer 560 on at least one of the first major surface 532 and the second major surface 534 of the substrate 530 at 902. Any suitable technique or techniques can be utilized to dispose the masking layer 560 on the substrate 530. At 904, the light source 580 can be disposed on the first major surface 532 of the substrate 530 such that the emission axis 582 of the light source is aligned with the first aperture 564 of the masking layer 560 in a direction orthogonal to the first major surface of the substrate. Any suitable technique or techniques can be utilized to dispose the light source 580 on the first major surface 532 of the substrate 530.

At 906, the detector 590 can be disposed on the first major surface 532 of the substrate 530 such that the detection axis 592 of the detector is aligned with the second aperture 566 of the masking layer 560 in the direction orthogonal to the first major surface of the substrate. Any suitable technique or techniques can be utilized to dispose the detector 590 on the first major surface 532 of the substrate 530. Further, the first major surface 532 of the substrate 530 can be hermetically sealed to the housing (not shown) using any suitable technique or techniques at 908.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed package, comprising:
 a housing comprising an inner surface and an outer surface;
 a substrate hermetically sealed to the housing and comprising a first major surface and a second major surface;
 a light source disposed on the first major surface of the substrate and comprising an emitting surface, wherein the light source is adapted to emit light through the first and second major surfaces of the substrate;
 a detector disposed on the first major surface of the substrate and comprising a detecting surface, wherein the detector is adapted to detect at least a portion of the light emitted by the light source; and
 a masking layer disposed on at least one of the first major surface and the second major surface of the substrate, wherein the masking layer comprises a first aperture aligned with an emission axis of the light source in a direction orthogonal to the first major surface of the substrate, wherein the masking layer further comprises a second aperture aligned with a detection axis of the detector in a direction orthogonal to the first major surface of the substrate.

2. The package of claim 1, wherein the masking layer is disposed on the first major surface, wherein the light source is disposed within the first aperture and the detector is disposed within the second aperture.

3. The package of claim 2, further comprising an insulation layer disposed such that masking layer is between the insulation layer and the first major surface of the substrate.

4. The package of claim 1, wherein the masking layer is disposed on the second major surface.

5. The package of claim 1, wherein the masking layer comprises a dielectric material.

6. The package of claim 1, wherein the masking layer comprises an electrically conductive material.

7. The package of claim 1, wherein the masking layer comprises a light absorbing material.

8. The package of claim 7, wherein the masking layer is adapted to absorb visible light.

9. The package of claim 7, wherein the masking layer is adapted to absorb near infrared light.

10. The package of claim 1, wherein the masking layer comprises columnar TiN.

11. The package of claim 1, further comprising an antenna disposed on the second major surface of the substrate.

12. The package of claim 11, wherein the antenna is disposed on a first portion of the second major surface of the substrate, wherein the light source is disposed such that the emission axis is aligned with a second portion of the second major surface of the substrate in a direction orthogonal to the first major surface of the substrate.

13. The package of claim 11, wherein the antenna comprises a first interstitial portion, wherein the detector is aligned with the first interstitial portion in a direction orthogonal to the first major surface of the substrate.

14. The package of claim 11, wherein the masking layer comprises an antenna seed layer disposed between the antenna and the second major surface of the substrate, wherein the antenna seed layer comprises a roughened surface.

* * * * *